United States Patent [19]

Brown, Jr. et al.

[11] Patent Number: 4,954,439
[45] Date of Patent: Sep. 4, 1990

[54] MULTIRIBBON MICROBIAL CELLULOSE

[75] Inventors: R. Malcolm Brown, Jr., Austin, Tex.; Fong C. Lin, Yun Lin Hsieu, Taiwan

[73] Assignee: Board of Regents, The University of Texas System, Austin, Tex.

[21] Appl. No.: 23,336

[22] Filed: Mar. 9, 1987

[51] Int. Cl.$^5$ .................. C12P 19/04; C08B 15/00; C12N 1/00
[52] U.S. Cl. ........................... 435/101; 536/30; 536/56; 536/127; 435/252.1; 435/823; 435/829; 435/878
[58] Field of Search ............... 435/101, 252.1, 823, 435/829, 878; 536/30, 56, 127

[56] References Cited

FOREIGN PATENT DOCUMENTS

A-0228779 7/1987 European Pat. Off. .
A-0260093 3/1988 European Pat. Off. .
88109956.8 3/1989 European Pat. Off. .

OTHER PUBLICATIONS

Brown et al., J. Applied Polymer Science, Applied Polymer Symposium 37:33–78 (1983).
Brown et al., Science, 218:1141–1142 (1982).
Haigler et al., Cellulose and Other Natural Polymer Systems, Malcolm Brown, Editor, Plyumpress, N.Y. (1982).
Haigler et al., J. Cell Biol., 94:64–69 (1982).
Brown, The Ekman-Days, 1981, 3:1–15 (1981).
1987 International Dissolving Pulps Conference; Sources of Cellulose: A Different Perspective; R. Malcolm Brown, Jr.; pp. 1–5.
Proc. Natl. Acad. Sci. USA, vol. 84, pp. 6985–6989, Oct. 1987; In vitro Synthesis of Cellulose II from a Cytoplasmic Membrane Fraction of . . . .
Journal of App. Polymer Sci.: Applied Polymer Symposium 37, 33–78 (1983); John Wiley & Sons, Inc.; The Biosynthesis and Degradation of Cellulose; R. Malcolm Brown, Jr. et al.
"Cellulose Chemistry and Its Applications", T. P. Nevell et al., Editors (1985).

*Primary Examiner*—Ronald W. Griffin
*Assistant Examiner*—Pamela S. Webber
*Attorney, Agent, or Firm*—Arnold, White & Durkee

[57] ABSTRACT

The present invention comprises a biologically pure culture of a cellulose-producing microorganism, preferably a prokaryote. This cellulose-producing microorganism is capable, during fermentation in an aqueous nutrient medium containing assimilable sources of carbon, nitrogen and inorganic substances, of reversal of direction of cellulose ribbon extrusion. This reversal of direction of cellulose ribbon extrusion results on the cellulose-producing microorganism shuttling, at least periodically, first in one direction and then in the other direction along a length of an earlier-deposited cellulose ribbon to add another cellulose ribbon thereto and produce a cellulose ribbon-bundle having a width of at least two cellulose ribbons.

The cellulose-producing microorganism of the present invention may be of the genus Acetobacter, Agrobacterium, Rhizobium, Pseudomonas or Alcaligenes, preferably of the genus Acetobacter and more preferably of the species *Acetobacter xylinum* or *Acetobacter pasteurianus*. Among preferred *Acetobacter xylinum* strains are strain N05, H1A; H1B; H1C; H2A; H2B; H5C; H5D; H6C; H8C; H8G; H14B; H15A; and H15B. *Acetobacter xylinum* strain N05, the most preferred strain, has identifying characterisitcs of ATCC 53582 on deposit with the American Type Culture Collection, Rockville, MD.

17 Claims, 5 Drawing Sheets

MULTIRIBBON MICROBIAL CELLULOSE

BACKGROUND OF THE INVENTION

The present invention relates to the observation that certain cellulose-producing microorganisms synthesize and extrude cellulose in a manner resulting in cellulose ribbon-bundles comprising multiple cellulose ribbons. Cellulose has long been known to be produced by certain microorganisms. The cellulose produced by most microorganisms is generally found to be an network of cellulose ribbons. A cellulose ribbon consists of numerous cellulose microfibrils, the number of microfibrils depending upon the size and type of microorganism. Each microfibril appears to contain about 40 glucan chains and to be formed from three cellulose protofibrils, while each protofibril is believed to be formed by the cluster of 10–15 glucan chains produced at each microbial cellulose synthetic site. The cellulose synthetic sites, located at least partially on the microbial surface, are linearly aligned.

SUMMARY OF THE INVENTION

The present invention comprises a biologically pure culture of a particular type of cellulose-producing and preferably prokaryotic microorganism. This cellulose-producing microorganism is capable, during growth in an aqueous nutrient medium containing assimilable sources of carbon, nitrogen and inorganic substances, or during a resting phase in an aqueous nutrient medium containing an assimilable source of carbon and inorganic substances, of repeated reversals of direction of cellulose ribbon extrusion. This reversal of direction of cellulose ribbon extrusion results in the cellulose-producing microorganism shuttling, at least periodically, in a first direction and then in a second direction along a length of an earlier-deposited cellulose ribbon to add another cellulose ribbon thereto and produce a cellulose ribbon-bundle having a width of at least two antiparallel cellulose ribbons.

The cellulose-producing microorganism of the present invention may be of the genus Acetobacter, Agrobacterium, Rhizobium, Pseudomonas or Alcaligenes, is preferably of the genus Acetobacter and more preferably of the species *Acetobacter xylinum*. Among preferred *Acetobacter xylinum* strains are strain NQ5; H1A; H1B; H1C; H2A; H2B; H5C; H5D; H6C; H8C; H8G; H14B; H15A; and H15B. *Acetobacter xylinum* strain NQ5, the most preferred strain, has identifying characteristics of ATCC 53582 deposited with the American Type Culture Collection, Rockville, MD on Jan. 27, 1987.

The cellulose ribbon-bundles produced by the cellulose-producing microorganism of the present invention may be characterized as comprising antiparallel cellulose ribbons having beta-1,4 linkages proceeding in a first direction alternating with cellulose ribbons having beta-1,4 linkages proceeding in an opposite direction. This alternating structure results from reversals in the direction of cellulose ribbon extrusion from a microorganism traveling along a previously deposited cellulose ribbon and depositing a new cellulose ribbon which becomes hydrogen-bonded to the adjacent earlier deposited cellulose ribbon.

The cellulose of the present invention is preferably produced by a cellulose-producing microorganism aerobically cultivated in an aqueous nutrient medium having a pH between about 3 and about 7 and at a temperature between about 20° C. and about 40° C.

The present invention involves a method for obtaining microbial cellulose having enhanced structural strength. The cellulose ribbon-bundles comprising multiple cellulose ribbons produced by the cultures of the present invention are stronger than the corresponding amount of single randomly dispersed cellulose ribbons. This method involves a nutrient medium comprising assimilable sources of carbon and inorganic salts (and nitrogen when growth is desired). The medium is incubated after an inoculation with a biologically pure culture of a cellulose-producing microorganism, capable, during incubation in said nutrient medium, of repeated reversals of direction of cellulose ribbon extrusion. Such directional reversals of extrusion as described above, result in said cellulose-producing microorganism shuttling, at least periodically, first in one direction and then in the other direction along a length of one or more earlier extruded cellulose ribbons to add another cellulose ribbon thereto. This process produces a cellulose ribbon-bundle being stronger than that produced by non-shuttling microorganisms. These ribbon-bundles have a width of at least two, and preferably three or more, cellulose ribbons. The cellulose thus produced may be collected for use or further processing, if desired. The microorganisms and conditions described above may be used to form this product cellulose comprising cellulose ribbon-bundles with cellulose ribbons of alternating antiparallel orientation, also described above. These antiparallel ribbon alignments result in glucan chain interrelationships reminiscent of cellulose II structure. This cellulose product of a reversal-type cellulose-producing microorganism may thus be a polymorph of cellulose I and cellulose II. The antiparallel ribbon alignment should result in one additional inter-ribbon hydrogen bond for each pair of interacting glucosic units. This additional hydrogen bond, along with the greater numbers of ribbons in a bundle, is consistent with a apparent greater physical strength observed.

The present invention also includes methods for identifying cellulose-producing microorganisms which, during fermentation in an aqueous nutrient medium containing assimilable sources of carbon, inorganic substances and also nitrogen when cell growth is desired periodically reverse their direction of cellulose ribbon extrusion such that said cellulose-producing microorganisms produce cellulose ribbon-bundles of multiple antiparallel ribbons. These methods may be used to select such a cellulose-producing microorganism for isolation and use in other processes of the present invention.

One method of identification comprises: (1) preparing a sterile aqueous nutrient medium containing assimilable sources of carbon, nitrogen and inorganic substances (nitrogen being optional for non-multiplying cells synthetisizing cellulose); (2) adding to said medium cellulose-producing microorganisms; (3) recording microscopic images of the cellulose-producing microorganisms in a sample of said inoculated medium under conditions of time-lapse video microscopy with a light microscope and dark field illumination, said recorded cellulose-producing microorganisms being in the act of cellulose synthesis and extrusion; and (4) determining, by examination of the continuously produced images, whether the cellulose-producing microorganisms shuttle, at least periodically, in a first direction and then in a second direction along a length of an earlier deposited cellulose ribbon to add another cellulose ribbon thereto and produce a cellulose ribbon-bundle comprising multiple cellulose ribbons, e.g., at least two antiparallel cellulose ribbons or at least three cellulose ribbons. The examination of the time-lapse images at a higher speed than they were recorded allows ready visualization of the above-mentioned cellulose-producing microorganism shuttling. Cellulose-producing microorganisms, not capable, during incubation in a nutrient medium, of reversal of direction of cellulose ribbon extrusion, usually produce a single cellulose ribbon and are not observed to shuttle back and forth along an earlier extruded cellulose ribbon.

A second method of identification involves electron microscopic examination of the cellulose product of cellulose-producing microorganisms. The cellulose-producing microorganism under investigation is treated in steps (1) and (2) as described above for the first method. A sample of the medium containing product cellulose is removed and placed on a grid for electron microscopy. The sample on the grid is dried and stained, preferably with a negative stain such as uranyl acetate. The stained sample is then subjected to transmission electron microscopy and electron micrographs obtained, preferably at magnifications from 10,000 to 20,000. The electron micrographs clearly show multiple-ribbon cellulose bundles from cellulose-producing microorganisms which repeatedly reverse their direction of cellulose ribbon extrusion. Cellulose-producing microorganisms incapable of periodic reversals of direction of cellulose extrusion usually result in assemblies of single cellulose ribbons, although multiple ribbon-bundles may sometimes be observed. Multiple cellulose ribbon-bundles from non-reversing organisms, when they are found, have parallel rather than antiparallel alignments.

While non-shuttling cellulose-producing microorganisms may sporadically produce bundles of parallel multiple cellulose ribbons, only cellulose-producing microorganisms capable, during incubation in nutrient medium, of repeated reversals of direction of cellulose ribbon extrusion characteristically and consistently produce cellulose ribbon-bundles comprising at least two or, more frequently, more than three cellulose ribbons. These latter ribbon-bundles may be further characterized by the anti-parallelism described above. The product cellulose, because of the anti-parallel inter-ribbon alignments present appears to be a polymorph of cellulose I and cellulose II.

In the present invention, the above-described methods have been applied to numerous strains of cellulose-producing *Acetobacter xylinum* strains. Strains observed to forgo reversals and produce typically low strength microbial cellulose include ATCC 23769, H1A, H6A, H7B, H9D and H10C. Strains capable of the reversals and producing a more birefringent and structurally stronger cellulose include NQ5, H1A, H1B, H1C, H2A, H2B, H5C, H5D, H6C, H8C, H8G, H14B, H15A and H15B.

DESCRIPTION OF THE PREFERRED EMBODIMENT

Figure 1:
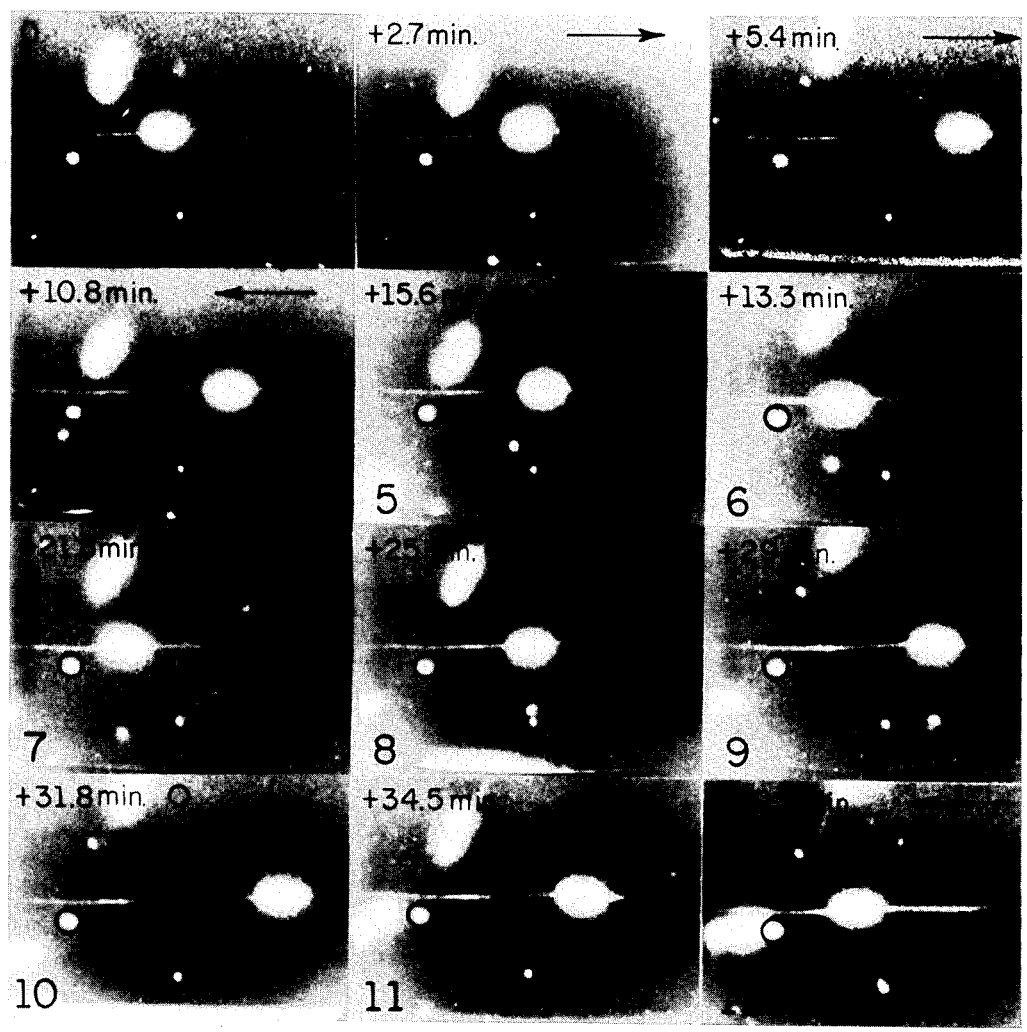
FIG. 1 shows a series of photographs taken from a time-lapse video tape (frames 1-12) of a cellulose-producing microorganism adding a cellulose ribbon during its shuttle in repeating reversals of direction along a previously deposited cellulose ribbon. The magnification is about 3,000× and the rate of cellulose production about one micron per minute.

When cellulose-producing microorganisms extrude a cellulose ribbon and the extruded cellulose ribbon becomes immobilized by attachment to a fixed object, the continued extrusion results in microbial movement. Certain cellulose-producing microorganisms have been found by the present inventiors to be capable of traveling parallel to one or more earlier-deposited cellulose ribbons while extruding a freshly synthesized cellulose ribbon which adheres to the earlier-deposited material. This phenomenon, particularly when the cellulose-producing microorganism is capable of periodically reversing its direction of travel along the earlier-deposited ribbon, results in formation of multiribbon cellulose ribbon-bundles.

The multiribbon cellulose ribbon-bundles characteristically produced by certain cellulose-producing microorganisms may be observed by staining, for example with uranyl acetate, and visualization by electron microscopy. The ribbon-bundles so visualized comprise tightly packed linearly aligned cellulose ribbons.

Cellulose-producing microorganisms useful in the present invention include members of the Acetobacter, Rhizobium, Agrobacterium, Pseudomonas and Alcaligenes genera (Brown et al. J. Applied Polymer Science Appl. Polymer Symp. (1983) V. 37 pp. 33-78). The growth of such cellulose-producing microorganisms and the synthesis of cellulose occur generally in a nutrient medium comprising assimilable sources of carbon nitrogen and inorganic matter. Cellulose synthesis may proceed in a nutrient medium comprising an assimilable source of carbon. The medium preferably has a pH between about 3.5 and about 7.0 and, when inoculated, is incubated under aerobic conditions and at preferable temperatures between about 20° C. and about 35° C. A use of *Acetobacter xylinum* to coat synthetic fibers with microbial cellulose is disclosed in U.S. Pat. No. 4,378,431, issued to Brown, which is incorporated by reference herein. Many varieties of cellulose-producing microorganisms, particularly *Acetobacter xylinum*, exist and are virtually ubiquitous in natural surroundings such as damp forests, for example.

A typical suitable nutrient medium for culture of cellulose-producing microorganisms is Schramm & Hestrin medium (Schramm et al., *J. General Microbiology*, Vol. 11, pp. 123-129, 1954) comprising about 20 g/l glucose; 5 g/l peptone; 5 g/l yeast extract; 2.7 g/l anhydrous dibasic sodium phosphate; and 1.15 g/l citric acid monohydrate. The pH of the medium is preferably adjusted to between about pH 3.5 and about pH 5.5 by the addition of acid. Another suitable nutrient medium comprises about 8 volume percent vinegar, 5 volume percent ethanol and 4 weight percent malt extract. Any of a wide variety of nutrient media having a pH between about 3 and about 7 are suitable for the practice of the present invention (see Bergey, cited below). Such suitable nutrient media may preferably include a hexose, most preferably glucose, acetic acid and yeast extract. Yet another suitable nutrient medium, adjusted to the above described pH range, is corn steep liquor. Also, resting cells, capable of producing cellulose, require only for example glucose and phosphate buffer for such production. When microbial growth is desired, a source of assimilable nitrogen should also be present.

According to Bergey's Manual of Systematic Bacteriology Vol. 1, (ed. N. R. Krieg, pp. 268-274, Williams and Wilkins, Baltimore, Md. 1984) cellulose synthesizing Acetobacter strains which were formerly classified as *Acetobacter aceti*, subspecies xylinum are now classified as subspecies of *Acetobacter pasteurianus* and *Acetobacter hansenii*. The strains of *Acetobacter xylinum* utilized herein may be synonymous with xylinum subspecies of *Acetobacter aceti*, *Acetobacter pasteurianus* or *Acetobacter hansenii*.

The following examples are intended to present the currently known best mode of practicing the present invention and to more fully enable one skilled in the art to practice the presently claimed invention. These examples are truly exemplary and illustrate the use of a preferred cellulose-producing microorganism in a preferred manner. Other cellulose-producing microorganisms and other cultivation conditions, for example, are capable of being substituted for those of the examples. The claims appended hereto are not limited by the specific contents of these examples unless otherwise specifically stated in those claims.

EXAMPLE 1

VISUALIZATION OF REVERSAL OF DIRECTION OF MICROBIAL CELLULOSE EXTRUSION

A sample of *Acetobacter xylinum*, strain NQ5 (deposited with the American Type Culture Collection, 12301 Parkland Drive, Rockville, MD 20852 U.S.A. on Jan. 27, 1987 as ATCC deposit number 53582) was inoculated into a quantity of Schramm/Hestrin nutrient medium and was aerobically cultured for 1-3 days at 28° C.

Generally, standing cultures work well. The resultant pellicle of cellulose was rapidly shaken, and the turbid suspension of cells released from the pellicle placed in fresh Schramm & Hestrin medium. A new pellicle was synthesized within several hours. Although not essential, this procedure ensures that a majority of the cells are active in cellulose synthesis. The new pellicle thus formed was gently shaken, and a suspension of cells placed in a drop of culture medium (in this case, Schramm & Hestrin) on a microscope slide. A cover slip was added.

For microscopy a Zeiss Universal Microscope was used, and darkfield optics were employed. For nondestructive observation of Acetobacter and the production of its cellulose, it is essential to use darkfield conditions. This was achieved by using an ultracondenser optically coupled to the lower surface of the microscope slide with immersion oil, and observed with a 40X oil immersion planapochromat objective with an aperture in the objective. A tungsten-halogen light source was used for observation, and a Dage Newvicon NC-65 SIT-tube (silicon intensified target) Camera was used to view the image. A Sony TVO-9000 Time Lapse Video Tape Recorder was used. Although not critical, it is preferable to use a timelapse video recording device because the reversals are more readily observed in playback mode when timelapse conditions have been employed. The video-recording device should have a single frame capability so that photographs can be made from the TV monitor of various segments of the video production. A time data generator is not essential, but is preferable and assists in documenting the events.

To produce the time lapse video sequence shown in FIG. 1, the above conditions and equipment were used, and the video tape recorder was set at a lapse speed of 1-48 hours. To reproduce FIG. 1, still frame shots were photographed from the monitor onto Kodak Tri-X film, and selected scenes reproduced.

FIG. 1 consists of twelve single frame samples (1-12), representing a total lapsed time of 39.9 minutes. In the first three frames, one cell is synthesizing a cellulose ribbon progressing from left to right. In frames 4-6, the direction of the ribbon synthesis is reversed, and the cell is moving from right to left. Note the improvement of light scattering by the celluose ribbon-bundle in frame 6 as contrasted with frame 4. An additional ribbon has been laid down adjacent to a previously synthesized ribbon, and this extra mass scatters more light. Frame 7 was taken just at the point of reversal at 21.8 minutes after frame 1 was captured. In frames 8 and 9, the cell is moving from the left to right. Compare the ribbon-bundles of frame 9 with those of frame 3. Two shuttling passes by the microorganism have added sufficient cellulose to increase the light scattering capacity of the ribbon mass as compared to that shown in frame 3. Frame 10 is 31.8 minutes into the synthesis phase, just at the end of a reversal. Frames 11 and 12 show the cell moving from right to left in the final scene. Note the cellulose mass to the right of the cell is now scattering more light than the cellulose to the left, after additionally laying down one more ribbon over that shown in frame 9. In all scenes, an immobile particle is circled for reference. Note also the reversal of an additional bacterium in the scene going from top to bottom of each figure. The data from frames 7 and 10 suggests a reversal cycle of approximately 10 minutes. Total magnification was about 3,000×. When *Acetobacter xylinum* strain 23769 from the American Type Culture Collection was studied under these conditions, no reversals of cellulose ribbon extrusion were seen observed.

EXAMPLE 2

ELECTRON MICROSCOPY OF CELLULOSE RIBBONS and BUNDLES THEREOF

*Acetobacter xylinum* strain 23769 from the American Type Culture Collection, Rockville, MD was cultured as described in Example 1 for strain NQ5 to produce cellulose. The bacteria were allowed to make cellulose for various periods of time ranging from 2-30 minutes. After the prescribed incubation period, a 300 mesh electron microscope grid coated with Formvar was brought face down to the surface of the liquid, whereupon a drop of the liquid containing the bacteria and cellulose was transferred to the Formvar surface. The excess solution was wicked off with Whatman #1 filter paper, and before drying, was rapidly replaced with a 2% solution of aqueous uranyl acetate. This was wicked off with Whatman #1 filter paper, and the grid was allowed to dry before being examined in a Philips 420 Transmission Electron Microscope (Eindhoven, Netherlands). The above specific procedures were applied to the Acetobacter, but any general negative staining preparation for electron microscopy should work as well as should any transmission electron microscope capable of resolving the structure shown. Scanning electron microscopy is not a preferred method because special drying techniques are required for preserving cellular structure. These techniques of microscopy can be performed by anyone accomplished or skilled in the art of transmission electron microscopy.

Figure 2A:
FIG. 2(A and B) shows electron micrographs of cellulose ribbons typically formed by a cellulose-producing microorganism extruding a single cellulose ribbon not in association with earlier formed ribbons.
Figure 2B:
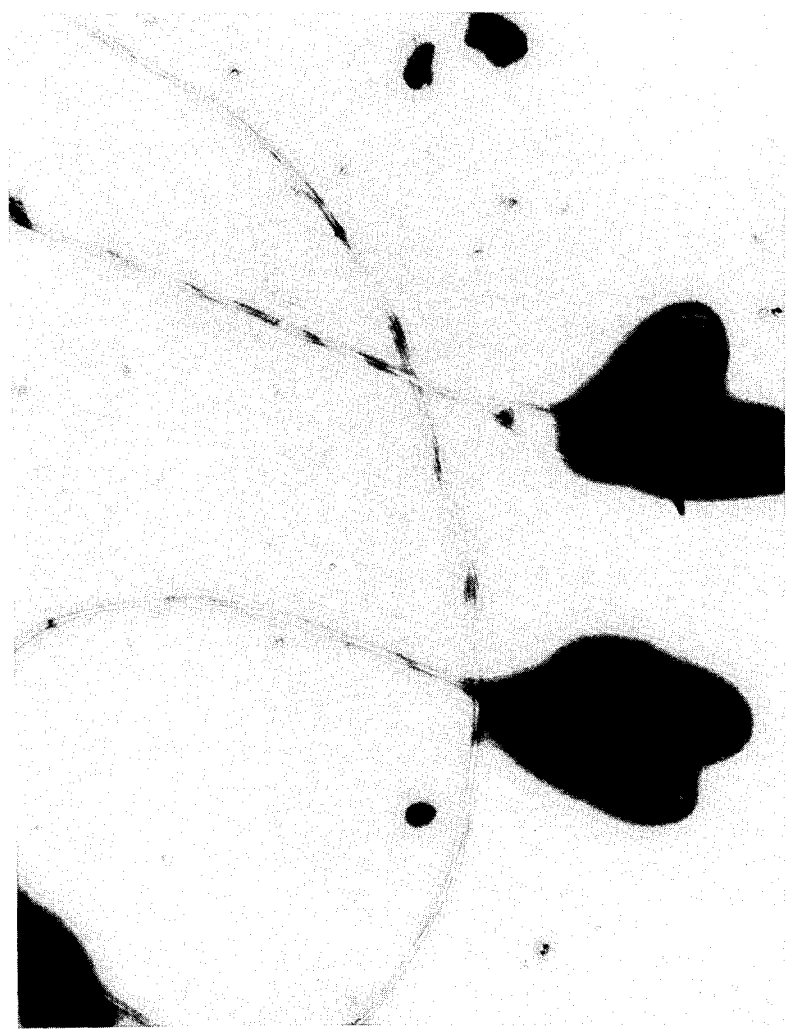

FIGS. 2A and 2B show electron micrographs resulting from these manipulations. As seen in FIG. 2A, the cellulose ribbons were not gathered into ribbon-bundles but were randomly distributed single cellulose ribbons. This cellulose configuration was consistent with the overt physical nature of the cellulose pellicle obtained from cellulose-producing microorganisms unable to migrate along an earlier deposited cellulose ribbon and reverse direction to form cellulose ribbon-bundles. The arrowhead in FIG. 2a designates a portion of amorphous cellulose probably resulting from the failure of cellulose microfibrils from an organism to crystallize into a cellulose ribbon.

FIG. 2B shows four cells extruding cellulose ribbons. These cells are in pairs, presumably the result of recent binary fissions and the ribbons of each pair intertwine to form a duo of parallel cellulose ribbons.

Figure 3A:
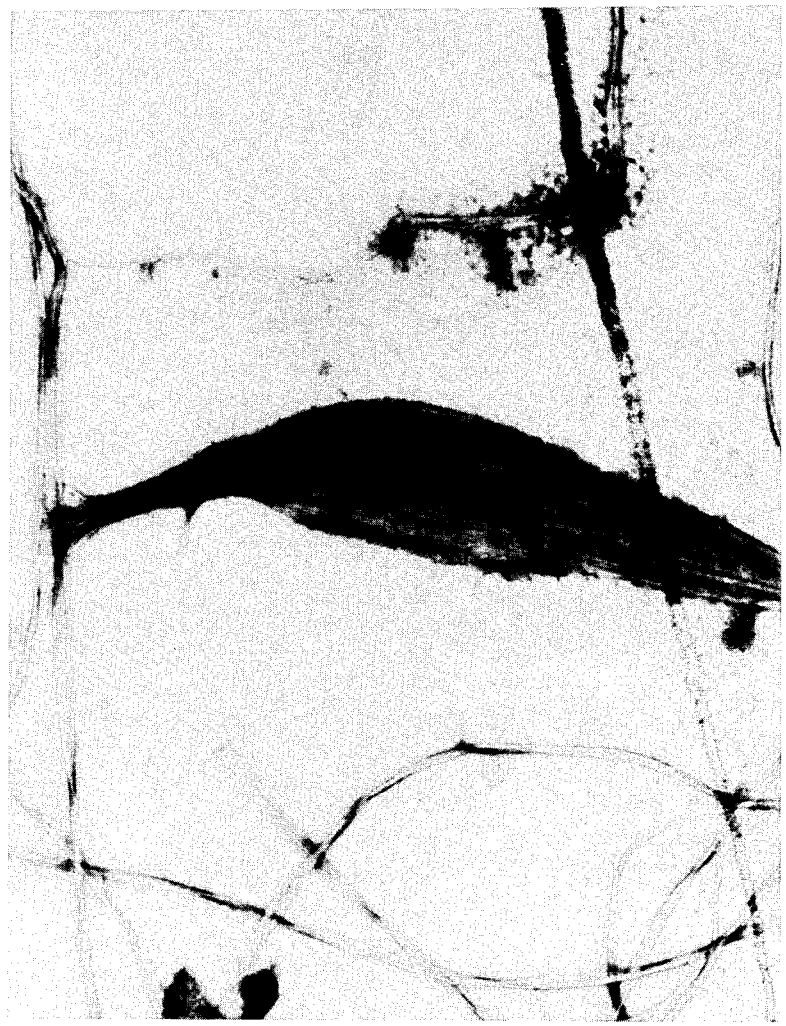
FIG. 3(A and B) shows an electron micrograph of cellulose ribbons from a cellulose-producing microorganism capable of reversing the direction of cellulose extrusion and forming cellulose ribbon-bundles.
Figure 3B:
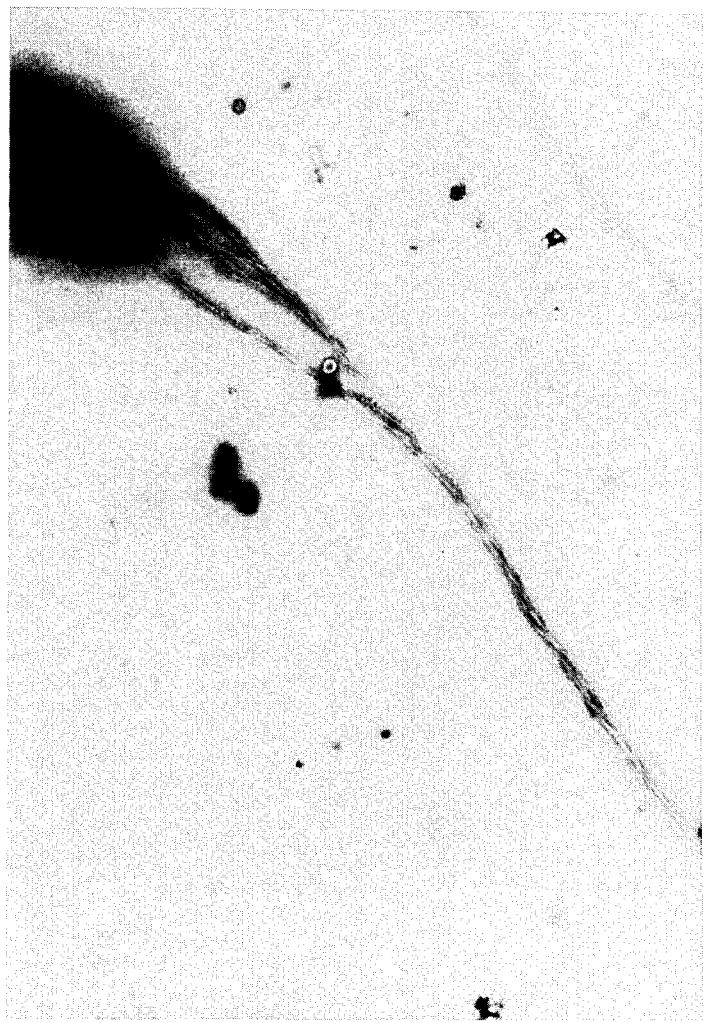

*Acetobacter xylinum* strain NQ5 (ATCC 53582), a firstly identified strain of the present invention, was cultured and treated in a likewise manner. FIGS. 3A and 3B show resulting electron micrographs. As shown in FIG. 3(A and B), ribbon-bundles of multiple cellulose ribbons were present. The formation of such ribbon-bundles are consistent the denser and more durable pellicle produced by cellulose-producing microorganisms capable of periodically reversing their paths of cellulose extrusion to form an antiparallel grid of cellulose ribbons. In FIG. 3A, a particularly thick cellulose-bundle (see structure designated by arrowhead) results from manifold short reversals. FIG. 3B shows a lengthier cellulose-bundle comprising less than about ten ribbons.

The reversals of direction extrusion result in a 180° turn for the cellulose ribbons involved. This drastic physical change must result in a finite point of breakdown in cellulose ribbon or microfibril crystallinity.

*Acetobacter xylinum* strain NQ5 is yet further characterized by its possession of a single circular plasmid. As determined on the basis of electrophoretic migration in agarose gel, this plasmid has a size of between about 45 and 55 kilobases.

The cellulose synthesized by reversing cellulose-producing microorganisms such as *Acetobacter xylinum* strain NQ5 results in a cellulosic pellicle which is stronger and considerably more durable than that produced by non-reversing strains. This durability is evident as increased tension and shearing strength. Such cellulose also exhibits high birefringence which is readily visualized by polarization microscopy using a first order red compensator and crossed polarizer and analyzer.

Changes may be made in the organisms and arrangement of the various elements such as nutrient media, steps and procedures described herein without departing from the concept and scope of the invention as defined in the following claims.

What is claimed is:

1. Cellulose produced by a biologically pure culture of a cellulose-producing microorganism, capable, during growth in an aqueous nutrient medium containing assimilable sources of carbon, nitrogen and inorganic substances, or during a resting phase in an aqueous nutrient medium containing an assimilable source of carbon and inorganic substances, of reversal of direction of cellulose ribbon extrusion such that said cellulose-producing microorganism shuttles, at least periodically, in a first direction and then in a second direction along a length of an earlier deposited cellulose ribbon to add another cellulose ribbon thereto and produce a cellulose ribbon-bundle comprising at least two antiparallel cellulose ribbons.

2. The cellulose of claim 1 wherein said cellulose-producing microorganism is of the genus Acetobacter, Agrobacterium, Rhizobium, Pseudomonas or Alcaligenes.

3. The cellulose of claim 1 wherein said cellulose-producing microorganism is of the genus Acetobacter.

4. The cellulose of claim 1 wherein said cellulose-producing microorganism is a subspecies of Acetobacter aceti, Acetobacter hansenii or Acetobacter pasteurianus.

5. The cellulose of claim 1 wherein said cellulose-producing microorganism is *Acetobacter xylinum* strain NQ5, having identifying characteristics of ATCC 53582 on deposit with the American Type Culture Collection, Rockville, MD.

6. Cellulose produced by a biologically pure culture of a cellulose-producing microorganism, capable, during growth in an aqueous nutrient medium containing assimilable sources of carbon, nitrogen and inorganic substances, or during a resting phase in an aqueous nutrient medium containing an assimilable source of carbon and inorganic substances, of reversal of direction of cellulose ribbon extrusion such that said cellulose-producing microorganism shuttles, at least periodically, in a first direction and then in a second direction along a length of an earlier deposited cellulose ribbon to add another cellulose ribbon thereto and produce a cellulose ribbon-bundle comprising at least three cellulose ribbons.

7. The cellulose of claim 6, wherein the cellulose ribbon-bundle is characterized as comprising cellulose ribbons having beta-1,4 linkages proceeding in a first direction alternating with cellulose ribbons having beta-1,4 linkages proceeding in an opposite direction.

8. The cellulose of claim 1, 2, 3, 4, 5 or 6 wherein the aqueous nutrient medium has a pH between about 3 and about 7.

9. The cellulose of claim 1, 2, 3, 4, 5 or 6 wherein the growth or resting phase is at a temperature between about 20° C. and about 40° C.

10. The cellulose of claim 1, 2, 3, 4, 5 or 6 wherein the growth or resting phase is aerobic.

11. The cellulose of claim 1, 2, 3, 4, 5 or 6 wherein the cellulose ribbon-bundle comprises at least three cellulose ribbons.

12. The cellulose of claim 1 or 6 defined further as being a polymorph of cellulose I and cellulose II.

13. Cellulose produced by a biologically pure culture of an Acetobacter species, capable, during growth in an aqueous nutrient medium containing assimilable sources of carbon, nitrogen and inorganic substances, or during a resting phase in an aqueous nutrient medium containing an assimilable source of carbon and inorganic substances, of reversing the direction of cellulose ribbon extrusion, said reversal causing said cellulose-producing microorganism to shuttle in a first direction and then in a second direction along a length of an earlier deposited cellulose ribbon while adding another cellulose ribbon thereto and producing a cellulose ribbon-bundle comprising at least two antiparallel cellulose ribbons.

14. Cellulose produced by a biologically pure culture of *Acetobacter xylinum* NQ5, ATCC 53582, capable, during growth in an aqueous nutrient medium containing assimilable sources of carbon, nitrogen and inorganic substances, or during a resting phase in an aqueous nutrient medium containing an assimilable source of carbon and inorganic substances, of reversal of direction of cellulose ribbon extrusion, said reversal causing said cellulose-producing microorganism to shuttle, at least periodically, in a first direction and then in a second direction along a length of an earlier deposited cellulose ribbon while adding another cellulose ribbon thereto and producing a cellulose ribbon-bundle comprising at least two antiparallel cellulose ribbons.

15. Cellulose characterized as having a ribbon-bundle structure comprising at least two anti-parallel cellulose ribbons having beta 1,4-linkages in a first direction alternating with beta 1,4-linkages in an opposite direction, said bundle structure further characterized as forming a plurality of hydrogen bonds conferring enhanced tension and shearing strength.

16. The cellulose of claim 15 further characterized as exhibiting a high birefringence.

17. The cellulose of claim 15 wherein the ribbon-bundle structure comprises at least three anti-parallel cellulose ribbons.

* * * * *